United States Patent [19]

Ikura et al.

[11] 4,187,302
[45] Feb. 5, 1980

[54] 1-[N-(4-CHLORO-2-TRIFLUOROMETHYL-PHENYL)PHENYLACETIMIDOYL]IMIDAZOLE, METAL COMPLEXES THEREOF, AND FUNGICIDAL COMPOSITIONS

[75] Inventors: Katsuyata Ikura, Ninomiya; Kiyoshi Katsuura; Masaaki Kataoka, both of Ohiso, all of Japan

[73] Assignee: Nippon Soda Company, Ltd., Tokyo, Japan

[21] Appl. No.: 886,358

[22] Filed: Mar. 14, 1978

[30] Foreign Application Priority Data

Mar. 31, 1977 [JP] Japan .................................. 52-35236

[51] Int. Cl.$^2$ ...................... A01N 9/22; A01N 11/04; C07D 233/56
[52] U.S. Cl. .................... 424/245; 548/341; 424/273 R; 548/109
[58] Field of Search .................. 260/299; 548/341; 424/273 R, 245

[56] References Cited

U.S. PATENT DOCUMENTS 3,993,469 11/1976 Regel et al. .............................. 71/92
4,080,462 3/1978 Brookes et al. ................. 424/273 R
4,085,209 4/1978 Miller et al. ......................... 424/245

FOREIGN PATENT DOCUMENTS 52-39674 3/1977 Japan ...................................... 548/341
52-46071 4/1977 Japan ...................................... 548/341

*Primary Examiner*—Mark L. Berch
*Attorney, Agent, or Firm*—George B. Oujevolk

[57] ABSTRACT

The compound of the formula and metal complexes thereof

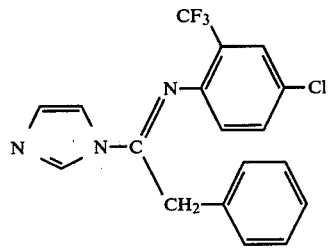

are useful as fungicide.

12 Claims, No Drawings

1-[N-(4-CHLORO-2-TRIFLUOROMETHYL-PHENYL)PHENYLACETIMIDOYL]IMIDAZOLE, METAL COMPLEXES THEREOF, AND FUNGICIDAL COMPOSITIONS

DETAILED DESCRIPTION OF THE INVENTION

The present invention relates to a novel imidazole derivative, 1-[N-(4-chloro-2-trifluoromethylphenyl)-phenylacetimidoyl]imidazole and metal complexes thereof, to a process for the preparation thereof and their uses as fungicides, in particular to a fungicidally active composition and method for controlling fungi.

It is disclosed in the Japanese published unexamined patent application No. 39674/77 that some imidazole derivatives have fungicidal activity. The imidazole derivatives are indicated by the general formula

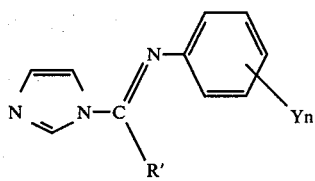

wherein R' is alkyl, Y is halogen, nitro, lower alkyl or lower alkoxy, and n is 0, 1 or 2.

Although these known imidazole derivatives have fungicidal activity, the activity is not sufficient and they cause phyto-toxicity to plants. Therefore these known compounds can not be put to practical use as fungicides.

It has been found that an imidazole derivative, 1-[N-(4-chloro-2-trifluoromethyl)phenylacetimidoyl]imidazole and metal complexes thereof, have outstanding fungicidal activity and cause no phyto-toxicity to plants.

The compounds of the present invention can be prepared by the reaction shown as follows:

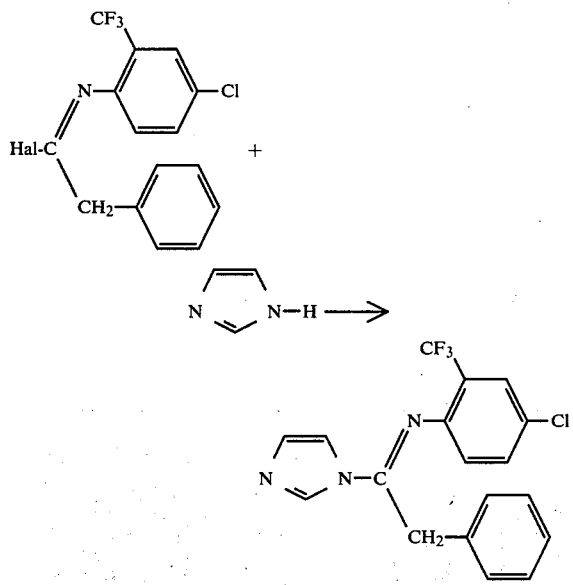

("Hal" represents halogen.)

The reaction is carried out in an inert solvent in the presence of an alkaline condensing agent such as sodium carbonate, potassium carbonate, sodium hydroxide, sodium methylalcoholate, trimethylamine, triethylamine, pyridine or piperidine. As an inert solvent, chloroform, dichloromethane, benzene, toluene, xylene, chlorobenzene, acetonitrile, acetone, dimethylsulfoxide, tetrahydrofuran, dimethylformamide or dioxane may be used. Ordinerily, a temperature from the range of 0 to the boiling point of the reaction solution, preferably a temperature from 40° C. to the boiling point, is satisfactory. The reaction is usually completed in 1 to 3 hours. After completion of the reaction, the reaction solution is washed with water and dried. The washing and drying may be carried out after replacing the solvent, if necessary. Then the solvent is distilled to obtain the desired compound.

Metal complexes of the present invention can be prepared by the following equation.

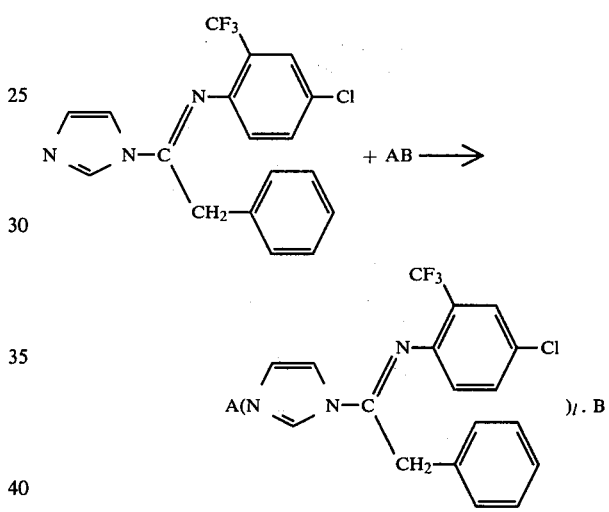

(AB is an organic or inorganic metal salt, A is bivalent or trivalent metal atom, B is anion component of the salt, and l corresponds to a number of valence of metal atom "A" in the metal salt "AB.")

As the metal salt, chloride, sulfate, nitrate or acetate of copper, zinc, nickel, cobalt, iron or silver is used. Copper sulfate, copper chloride, zinc chloride or zinc acetate is preferably used. When carring out the reaction for the preparation of the metal complexes, the imidazole derivative is dissolved in an inert solvent and a metal salt is added thereto and the mixture is stirred to allow to react. The reaction is ordinarily carried out at a room temperature for several minutes. As an inert solvent, any solvents which dissolve the imidazole derivative and are miscible with water can be used.

Ordinarily, ethyl acetate, methanol, acetonitrile, dioxane or tetrahydrofuran is used. After completion of the reaction, the reaction mixture is poured into n-hexane or water and the precipiated crystal is removed from it by filtration to obtain the metal complex of the present invention.

The following are examples of preparation of compound of the present invention.

EXAMPLE 1

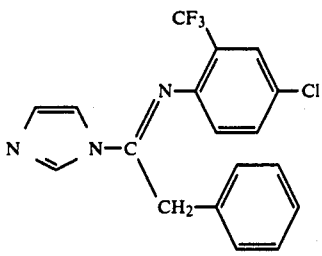

3.5 g of N-(4-chloro-2-trifuluoromethylphenyl)-phenylacetamide were allowed to react with 2.6 g of phosphorus pentachloride in 40 ml of benzene by refluxing the mixture. After completion of the reaction, benzene and phosphorus oxychloride were evaporated. The resulting N-(4-chloro-2-trifluoromethylphenyl)-phenylacetimidoyl chloride was dissolved in 50 ml of acetonitrile and 0.85 g of imidazole were added thereto with stirring.

To the resulting solution were gradually added 1.3 g of triethylamine with cooling and the solution was maintained for 30 minutes at 60° C. After removal of acetonitrile by distillation, the residue was dissolved in 60 ml of dichloromethane and the solution was washed with water and then dried. An oily product obtained by distillation of dichloromethane from the solution was purified by silicagel column chromatography to obtain 2.1 g of the desired compound. ($n_D^{28}$ 1.5818)

EXAMPLE 2

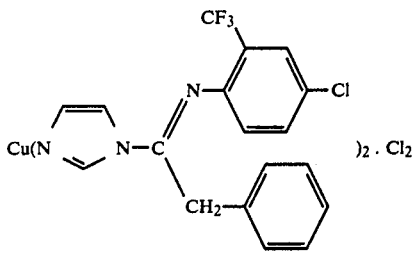

2 g of 1-[N-(4-chloro-2-trifuluoromethyl)-phenylacetimidoyl]imidazole were dissolved in 5 ml of ethyl acetate and 0.5 g of anhydrous copper chloride were added thereto. After leaving the mixture for 5 minutes at room temperature, it was poured into 100 ml of n-hexane to precipitate crystals. The crystals were washed with n-hexane several times and dried under reduced pressure to obtain 2 g of the desired metal complex. (m.p. 105°–108° C.)

Examples of compounds of the present invention are listed in Table 1.

Table 1

| Compound No. | Structural Formula | Physical Constant |
|---|---|---|
| 1 | ![structure] CF₃, Cl, imidazole-N=C-CH₂-phenyl | $n_D^{28}$ 1.5818 |
| 2 | Cu(N imidazole N—C(=N-Ar)CH₂Ph)₂ · Cl₂ | m.p. 105–108 |
| 3 | Zn(N imidazole N—C(=N-Ar)CH₂Ph)₂ · (CH₃COO)₂ | m.p. 42–46 |

As mentioned previously, it has been found that compounds of the present invention possess fungicidal activity when employed to prevent damage to plants.

Such compounds may control a wide variety of fungus diseases to foliage, fruit, stems and roots of growing plants, without damage to the host.

The many fungi against which such compounds are active may be represented by, but is not intended to be limited to, the following:

gray mold, sclerotia rot, damping-off and powdery mildew of vegetables, brown rot of peach, leaf spot of corn, scab of apple and pear, rust of pear, powdery mildew of apple, and rust of cereals; and the compounds are particularly effective against powdery mildew, scab and rust.

It is another advantage that such compounds cause no phyto-toxicity to plants.

The method of the present invention includes the employment of a liquid or solid composition containing one or more of the compounds as an active component.

The compound may be used directly without mixing with suitable carriers. The active ingredient of a fungicidal composition exemplifying the invention may be formulated by mixing the suitable carriers in a form generally used in pesticidal compositions, such as wettable powder, emulsifiable concentrate, dust formulation, granular formulation, water soluble powder and aerosol. As solid carriers, bentonite, diatomaceous earth, apatite, gypsum, talc, pyrophyllite, vermiculite and clay, for example, may be used. As liquid carriers, kerosene, mineral oil, petroleum, solvent naphtha, xylene, cyclohexane, cyclohexanone, dimethylformamide, dimethylsulfoxide, alcohol, acetone, benzene and water, for example, may be used. If so desired, a surface active agent may be added in order to give a homogeneous and stable formulation.

The concentration of the active ingredient in the fungicidal composition may vary according to type of formulation, and is for example, 5 to 80 weight percent, preferably 20 to 80 weight percent, in wettable powders; 5 to 70 weight percent, preferably 10 to 50 weight percent, in emulsifiable concentrates; and 0.5 to 20 weight percent, preferably 1 to 10 weight percent, in dust formulations.

A wettable powder or an emulsifiable concentrate containing a quantity of the active compound may be suspended or emulsified in water and then sprayed on the foliage of plants or on the locus to be protected.

Furthermore, the compounds may be used in mixture with other fungicides, insecticides, acaricides and herbicides.

Some non-limiting examples of fungicidal compositions according to the invention are as follows:

EXAMPLE 3

| Wettable Powder | Parts by weight |
|---|---|
| Compound No. 1 | 40 |
| Diatomaceous earth | 53 |
| Higher alkyl sulfate | 4 |
| Alkylnaphthalene sulfonic acid | 3 |

These are mixed homogeneously and reduced to fine particles to provide a wettable powder containing 40% of the active ingredient. In use, the powder is diluted to a desired concentration with water and is sprayed as a suspension.

EXAMPLE 4

| Emulsifiable Concentrate | Parts by weight |
|---|---|
| Compound No. 2 | 30 |
| Xylene | 33 |
| Dimethylformamide | 30 |

| -continued Emulsifiable Concentrate | Parts by weight |
|---|---|
| Polyoxyethylene alkylallylether | 7 |

These are mixed and dissolved to provide an emulsifiable concentrate containing 30% of the active ingredient. In use, the concentrate is diluted to a desired concentration with water and then is sprayed as an emulsion.

EXAMPLE 5

| Dust Formulation | Parts by weight |
|---|---|
| Compound No. 3 | 10 |
| Talc | 89 |
| Polyoxyethylene alkylallylether | 1 |

These are mixed homogeneously and reduced to fine particles to provide a dust formulation containing 10% of the active ingredient. In use, the formulation is applied directly.

The fungicidal activity of compounds of this invention is illustrated by the following tests:

Test 1

Test for Control of Gray Mold of Bean

The detached leaves of kidney beans (*Phaseolus vulgaris*) were immersed for about 30 seconds in an aqueous suspension prepared by diluting a wettable powder to a concentration of 200 ppm of a test compound. After air-dried, the treated leaves were inoculated with mycelia of *Botrytis cinerea* and kept at 20° C. in a moist chamber. Control effect was checked 4 days after inoculation. The results are shown in Table 2.

Test 2

Test for Control of Cucumber Powdery Mildew

The leaves of potted cucumber seedlings (variety: Satsukimidori) at 1-2 leaf stage were sprayed with an aqueous suspension (5 ml/pot) prepared by diluting a wettable powder to a concentration of 100 ppm of a test compound. After air-dried, the treated leaves were inoculated with conidia of *Sphaerotheca fuliginea and kept for* 9 days at 25° C. in a greenhouse. Then, control effect was checked. The results are shown in Table 2.

Test 3

Test for Control of Rhizoctonia Damping-off of Cucumber

Cucumber seedlings (variety: Suyo) at the cotyledon stage were treated by injecting an aqueous suspension containing a test compound at 100 ppm into the soil (10 ml/pot with 7 seedlings) after inoculated with mycelia of *Rhizoctonia solani*. Control effect was evaluated 4 days after inoculation. The results are shown in Table 2.

Table 2

| Compound No. | Control Value (%) | | |
|---|---|---|---|
| | Test 1 | Test 2 | Test 3 |
| 1 | 100 | 100 | 100 |
| 2 | 96 | 100 | |

Table 2-continued

| Compound No. | Control Value (%) | | |
|---|---|---|---|
| | Test 1 | Test 2 | Test 3 |
| 3 | | 100 | |
| Comparative Compound* | | | |
| 1 | | 63 | 0** |
| 2 | 90 | | |
| 3 | | 90 | |
| 4 | | | 90 |
| untreated | 0 | 0 | 0 |

*Comparative Compound

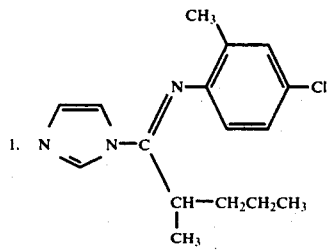

Japanese published unexamined patent application No. 39674/77

2. Euparen: N'-dichlorofluoromethylthio-N,N-dimethyl-N'-phenylsulfamide

3. Morestan: 6-methyl-1,3-dithiolo[4,5-b]quinoxalin-2-one

4. PCNB: Pentachloronitrobenzene

**Phyto-toxicity was observed.

We claim:

1. 1-[N-(4-chloro-2-trifluoromethylphenyl)-phenylacetimidoyl]imidazole

2. A metal complex of the formula wherein A is Cu(II) or Zn(II) and B is cl$_2$ or (CH$_3$COO)$_2$.

3. The metal complex which is bis[1-{N-(4-chlorotrifluoromethylphenyl)phenylacetimidoyl{imidazole].-copper chloride 4. The metal complex which is bis[1-{N-(4-chlorotrifluoromethylphenyl)phenylacetimidoyl}imidazole].-zinc acetate 5. A fungicidal composition comprising an inert carrier and a fungicidally effective amount of the compound of claim 1.

6. A fungicidal composition comprising an inert carrier and a fungicidally effective amount of the compound of claim 2.

7. A fungicidal composition comprising an inert carrier and a fungicidally effective amount of the compound of claim 3.

8. A fungicidal composition comprising an inert carrier and a fungicidally effective amount of the compound of claim 4.

9. A method for the control of fungi comprising applying to the locus to be protected an effective amount of the compound of claim 1.

10. A method for the control of fungi comprising applying to the locus to be protected an effective amount of the compound of claim 2.

11. A method for the control of fungi comprising applying to the locus to be protected an effective amount of the compound of claim 3.

12. A method for the control of fungi comprising applying to the locus to be protected an effective amount of the compound of claim 4.